United States Patent [19]

Reiser et al.

[11] Patent Number: 4,501,897
[45] Date of Patent: Feb. 26, 1985

[54] PROCESS FOR THE PREPARATION OF E-ISOMERS OF 1-CYCLOHEXYL-2-(1,2,4-TRIAZOL-1-yl)-1-PENTEN-3-ONE DERIVATIVES

[75] Inventors: Wolf Reiser; Hans-Ludwig Elbe, both of Wuppertal; Peter Feyen, Mettmann, all of Fed. Rep. of Germany

[73] Assignee: Bayer Aktiengesellschaft, Leverkusen, Fed. Rep. of Germany

[21] Appl. No.: 523,537

[22] Filed: Aug. 16, 1983

[30] Foreign Application Priority Data

Aug. 21, 1982 [DE] Fed. Rep. of Germany ....... 3231205

[51] Int. Cl.³ .......................................... C07D 249/08
[52] U.S. Cl. .................................................. 548/262
[58] Field of Search ......................................... 548/262

[56] References Cited

FOREIGN PATENT DOCUMENTS

| | | | |
|---|---|---|---|
| 0015387 | 9/1980 | European Pat. Off. ............ | 548/262 |
| 0140978 | 11/1981 | Japan ................................... | 424/269 |
| 2046260 | 11/1980 | United Kingdom ................. | 424/269 |

*Primary Examiner*—Alton D. Rollins
*Attorney, Agent, or Firm*—Sprung, Horn, Kramer & Woods

[57] ABSTRACT

A process for the preparation of E-isomers of 1-cyclohexyl-2-(1,2,4-triazol-1-yl)-1-penten-3-one derivatives of the formula

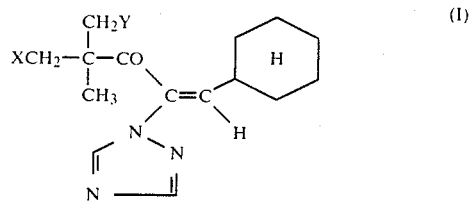

in which X and Y independently of one another represent hydrogen or halogen by contacting isomers of 1-cyclohexyl-2-(1,2,4-triazol-1-yl)-1-penten-3-one derivatives of the formula

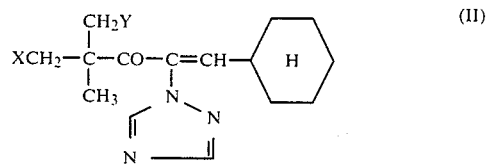

in which X and Y have the previously indicated meaning with at least one secondary amine, if desired in the presence of water and/or in the presence of a water immiscible solvent.

11 Claims, No Drawings

PROCESS FOR THE PREPARATION OF E-ISOMERS OF 1-CYCLOHEXYL-2-(1,2,4-TRIAZOL-1-yl)-1-PENTEN-3-ONE DERIVATIVES

The present invention relates to a new process for the preparation of known plant growth-regulating and fungicidally active E-isomers of 1-cyclohexyl-2-(1,2,4-triazol-1-yl)-1-penten-3-one derivatives.

It has already been disclosed that 1-cyclohexyl-2-(1,2,4-triazol-1-yl)-1-penten-3-one derivatives are obtained if cyclohexanealdehyde is reacted with appropriate triazolyl ketones in the presence of a basic catalyst, such as, for example, piperidine acetate, and in the presence of an inert organic solvent, in particular an (aromatic) hydrocarbon, at the boiling point of the particular solvent.

The isolation of the end products, and in this case, in particular, the isolation of the different isomers, is preferably effected via the acid addition salts of the latter (compare EP-OS (European Published Specification) No. 15,387).

This process has the disadvantage that the preparation of pure isomers, such as, in particular, the E-isomers, is effected in a manner which is unfavourable from the economic point of view. Thus the liberation of the appropriate pure isomer from the corresponding acid addition salt by means of a base, such as, for example, sodium carbonate, requires a change of solvent, and the yields of desired isomeric product are, in general, unsatisfactory.

It has now been found that the known E-isomers of 1-cyclohexyl-2-(1,2,4-triazol-1-yl)-1-penten-3-one derivatives of the formula

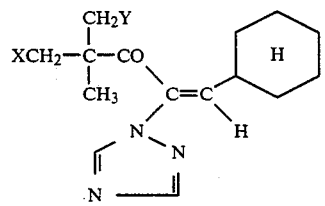

in which X and Y independently of one another represent hydrogen or halogen, are obtained if the mixtures of isomers of 1-cyclohexyl-2-(1,2,4-triazol-1-yl)-penten-3-one derivatives of the formula

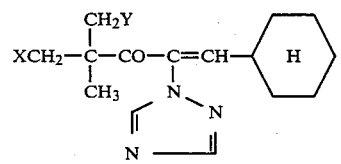

in which X and Y have the meaning indicated above, are reacted with secondary amines, if appropriate in the presence of water and/or in the presence of a water-immiscible solvent.

It must be described as surprising that the mixtures of isomers of compounds of the formula (II) can be isomerized, in the process according to the invention, to give the E-isomers of compounds of the formula (I) in very good yields.

The process according to the invention thus has the advantage that it is possible to obtain the E-isomers of compounds of the formula (I) in a simple manner and in very good yields.

The E-isomers of 1-cyclohexyl-2-(1,2,4-triazol-1-yl)-1-penten-3-one derivatives which can be prepared by the process according to the invention are defined in a general manner by the formula (I). In this formula, X and Y independently of one another preferably represent hydrogen, fluorine, chlorine or bromine.

Compounds of the formula (I) which are particularly preferred are those in which X represents hydrogen and Y represents hydrogen, fluorine or chlorine.

If, for example, the mixture of isomers of 1-cyclohexyl-4,4-dimethyl-2-(1,2,4-triazol-1-yl)-1-penten-3-one and piperidine are used as starting materials, the course of the reaction can be represented by the following equation:

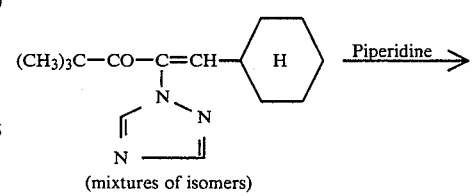

(mixtures of isomers)

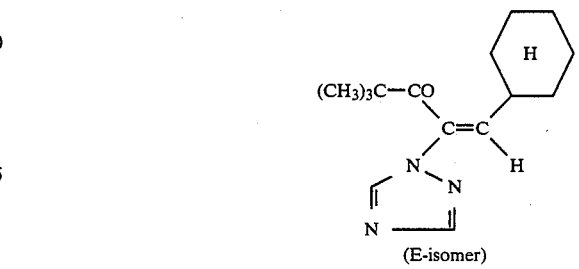

(E-isomer)

The mixtures of isomers of 1-cyclohexyl-2-(1,2,4-triazol-1-yl)-penten-3-one derivatives to be used as starting materials in carrying out the process according to the invention are defined in a general manner by the formula (II). In this formula, X and Y preferably represent the radicals which have already been mentioned preferentially for these substituents in connection with the description of the substances of the formula (I) which can be prepared in accordance with the invention.

The mixtures of isomers of the formula (II) are known (compare EP-OS (European Published Specification) No. 15,387).

The reaction according to the invention is carried out using secondary amines. In this connection it is possible to employ any secondary amines which can customarily be used. Piperidine, pyrrolidine, dimethylamine or diethylamine are preferentially suitable.

The reaction according to the invention can be carried out, if appropriate, in the presence of water and/or a water-immiscible solvent. This includes, preferably, aliphatic, cycloaliphatic and aromatic hydrocarbons, such as, for example, cyclohexane, petroleum ether, toluene, isododecane, isooctane or ligroin.

The reaction according to the invention is preferably carried out at temperatures between −30° and +30° C.

In carrying out the reaction according to the invention, it is preferable to employ a catalytic amount or even up to 0.5 mol of secondary amine for 1 mol of the mixture of isomers of the formula (II). The isolation of the end products is effected in a manner which is generally customary.

The substances which can be prepared in accordance with the invention are distinguished, as is known, by a good plant growth-regulating and fungicidal activity (compare EP-OS (European Published Specification) No. 15,387). In addition, they can be employed as intermediate products for the preparation of further plant growth-regulating and fungicidal compounds, for example by customary reduction of the keto group (compare EP-OS (European Published Specification) No. 15,387).

The process according to the invention will be illustrated with the help of the following preparation examples:

PREPARATION EXAMPLES

EXAMPLE 1

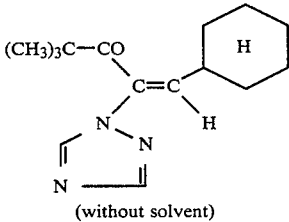

(without solvent)

17 g (0.2 mol) of piperidine are added dropwise, at room temperature and while stirring vigorously, to 130 g (0.5 mol) of the mixture of isomers of 1-cyclohexyl-4,4-dimethyl-2-(1,2,4-triazol-1-yl)-penten-3-one (consisting of 29% of E-isomer, 69% of Z-isomer and 2% of isomers in which the double bond has been shifted), the reaction mixture solidifying, with evolution of heat, to form a mash of crystals. The reaction mixture is allowed to stand for 2 hours, 100 ml of n-pentane are then added and the mixture is stirred up. After cooling, the finely crystalline solid is separated off and washed with a little cold n-pentane until it is free from amine. 100 g (77% of theory) of the pure E-isomer of 1-cyclohexyl-4,4-dimethyl-2-(1,2,4-triazol-1-yl)-1-penten-3-one, melting point 97°–98° C., are obtained. (in the presence of water)

130 g (0.5 mol) of the mixture of isomers of 1-cyclohexyl-4,4-dimethyl-2-(1,2,4-triazol-1-yl)-1-penten-3-one (consisting of 29% of E-isomer, 69% of Z-isomer and 2% of isomers in which the double bond has been shifted) are added, while stirring vigorously, to a solution of 20 ml of 30% strength aqueous dimethylamine and 100 ml of water. The emulsion, which is at first oily, solidifies in the course of about 2 hours and can then be filtered with suction. The residue is washed several times with water, dried and taken up in 100 ml of n-pentane. The finely crystalline precipitate is filtered off with suction and dried. 98 g (75.4% of theory) of a pure E-isomer of 1-cyclohexyl-4,4-dimethyl-2-(1,2,4-triazol-1-yl)-1-penten-3-one, melting point 98° C., are obtained.

What is claimed is:

1. A process for the preparation of an E-isomer of 1-cyclohexyl-2,2(1,2,4-triazol-1-yl)-1-penten-3-one of the formula

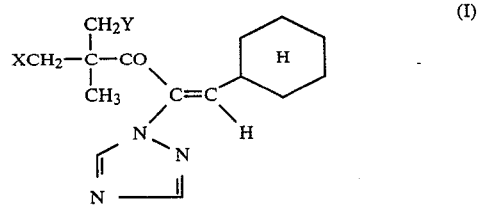

wherein X and Y independently of one another represent hydrogen or halogen which comprises contacting a mixture of isomers of 1-cyclohexyl-2-(1,2,4-triazol-1-yl)-1-penten-3-one of the formula

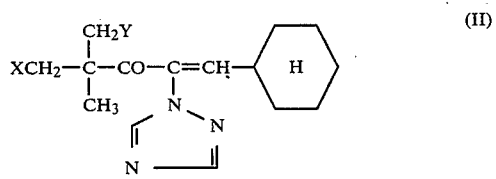

wherein X and Y have the previous indicated meaning, with at least one secondary amine.

2. A process according to claim 1 wherein the process is carried out in the presence of water.

3. A process according to claim 1 wherein the process is carried out in the presence of a water immiscible solvent.

4. A process according to claim 1, wherein the secondary amine employed is piperidine, pyrrolidine, dimethylamine or diethylamine.

5. A process according to claim 3, wherein the water immiscible solvent is an aliphatic, cycloaliphatic or aromatic hydrocarbon.

6. A process according to claim 5, wherein said water immiscible solvent is n-pentane.

7. A process according to claim 1, wherein the process is carried out at a temperature between −30° and +30° C.

8. A process according to claim 1, wherein the secondary amine is present in an amount between a catalytic amount and up to 0.5 mol of secondary amine per mol of a mixture of isomers of formula (II).

9. A process according to claim 1, wherein the secondary amine is piperidine and said piperidine is added to a mixture of isomers of 1-cyclohexyl-4,4-dimethyl-2-(1,2,4-triazol-1-yl)-penten-3-one and thereafter n-pentane, is added to the resultant mixture from which is recovered the pure E-isomer thereof.

10. A process according to claim 1, wherein the secondary amine is dimethylamine, a mixture of isomers of 1-cyclohexyl-4,4-dimethyl-2-(1,2,4-triazol-1-yl)-1-penten-3-one is added to an aqueous solution of said dimethylamine, and pure E-isomer of 1-cyclohexyl-4,4-dimethyl-2-(1,2,4-triazol-1-yl)-penten-3-one which has solidified is taken up in a water immiscible solvent.

11. A process according to claim 10, wherein said water immiscible solvent is n-pentane.

* * * * *